United States Patent
Takayama

(10) Patent No.: US 11,732,310 B2
(45) Date of Patent: Aug. 22, 2023

(54) DNA CHIP FOR DETECTING DENTAL CARIES BACTERIA

(71) Applicant: GC CORPORATION, Sunto-gun (JP)

(72) Inventor: Kazuto Takayama, Tokyo (JP)

(73) Assignee: GC CORPORATION, Sunto-gun (JP)

( * ) Notice: Subject to any disclaimer, the term of this patent is extended or adjusted under 35 U.S.C. 154(b) by 445 days.

(21) Appl. No.: 16/493,082

(22) PCT Filed: Mar. 13, 2018

(86) PCT No.: PCT/JP2018/009620
§ 371 (c)(1),
(2) Date: Sep. 11, 2019

(87) PCT Pub. No.: WO2018/168816
PCT Pub. Date: Sep. 20, 2018

(65) Prior Publication Data
US 2020/0377931 A1    Dec. 3, 2020

(30) Foreign Application Priority Data

Mar. 14, 2017 (JP) ................................. 2017-048654

(51) Int. Cl.
*C12Q 1/68* (2018.01)
*C07H 21/04* (2006.01)
*C12Q 1/689* (2018.01)

(52) U.S. Cl.
CPC .................................... *C12Q 1/689* (2013.01)

(58) Field of Classification Search
None
See application file for complete search history.

(56) References Cited

U.S. PATENT DOCUMENTS

| | | | | |
|---|---|---|---|---|
| 6,582,908 B2 * | 6/2003 | Fodor | ................... | B01J 19/0046 435/288.3 |
| 2007/0269813 A1 * | 11/2007 | Dewhirst | ............... | C12Q 1/689 435/6.11 |
| 2008/0182265 A1 | 7/2008 | Matsumoto | | |
| 2018/0148769 A1 * | 5/2018 | Hara | ...................... | C12Q 1/689 |

FOREIGN PATENT DOCUMENTS

| JP | 2008-206516 A | | 9/2008 | |
|---|---|---|---|---|
| JP | 2015-231362 A | | 12/2015 | |
| JP | 2017-23093 | * | 2/2017 | ............... C12Q 1/68 |
| JP | 2017-23093 A | | 2/2017 | |
| WO | WO200198781 | * | 12/2001 | ............. G01N 33/53 |
| WO | WO 03/106676 A1 | | 12/2003 | |
| WO | WO 2016/129249 A1 | | 8/2016 | |

OTHER PUBLICATIONS

NEB catalog (1998/1999), pp. 121,284. (Year: 1998).*
Office Action dated Jul. 27, 2021 in corresponding Japanese Patent Application No. 2017-048654 (with English Translation), 7 pages.
International Search Report dated Jun. 19, 2018 in PCT/JP2018/009620, 2 pages.
Extended European Search Report dated Nov. 11, 2020 in corresponding European patent application No. 18768077.2, 7 pages.
Christophe Lay et al., "Design and Validation of 16S rRNA Probes to Enumerate Members of the *Clostridium leptum* Subgroup in Human Faecal Microbiota", Environmental Microbiology, Blackwell Science, GB, vol. 7, No. 7, XP002623953, Jul. 1, 2005, pp. 933-946.
J. Replies et al., "A DNA Microarray Platform Based on Direct Detection of rRNA for Characterization of Freshwater Sediment-Related Prokaryotic Communities", Applied And Environmental Microbiology, vol. 72. No. 7. XP055111680. Jul. 1, 2006, pp. 4829-4838.
Gross, L. Erin et al., "Beyond *Streptococcus mutans*: Dental Caries Onset Linked to Multiple Species by 16S rRNA Community Analysis", Plos One. 2012, vol. 7, Issue 10, pp. 1-11.
Pontigo, F. et al., "Molecular Phylogeny and a Taxonomic Proposal for the Genus *Streptococcus*", Genetics and Molecular Research, 2015, vol. 14, No. 3, pp. 10905-10918, table 1.
Fusao Nishikawaraa et al., "Evaluation of Cariogenic Bacteria", European Journal of Dentistry, Jan. 2007, vol. 1, pp. 31-39.

(Continued)

*Primary Examiner* — Jeanine A Goldberg

(74) *Attorney, Agent, or Firm* — Oblon, McClelland, Maier & Neustadt, L.L.P.

(57) ABSTRACT

Provided is a means/method with which it is possible to quickly and efficiently detect bacteria that cause dental caries and evaluate dental caries. The present invention pertains to a DNA chip, etc., that carries, for example, the following probe (a) and at least one probe from among the following probes (b) and (c). (a) A probe comprising a nucleic acid that hybridizes to 16S rRNA specific to each of one or more oral bacteria to be detected, wherein the probe is any of the following sequences (i)-(iii): (i) at least one sequence selected from nucleotide sequences represented by SEQ ID NOS: 2-7; (ii) a complementary sequence of a sequence of (i); or (iii) a sequence substantially identical to a sequence of (i) or (ii). (b) A total amount indicator probe. (c) An absolute amount indicator probe of one type or a plurality of types.

13 Claims, No Drawings

Specification includes a Sequence Listing.

(56) References Cited

OTHER PUBLICATIONS

S. Alaluusua et al., "Oral Colonization by More Than One Colonal Type of Mutans *Streptococcus* in Children with Nursing-bottle Dental Caries", Archives of Oral Biology.1996,vol. 41, pp. 167-173.
Noboru Kaneko et al., "pm205, Relationship Between Detection Rate of Mutans *Streptococcus* and Dental Caries in Japanese Elementary School Children", Japanese Journal of Bacteriology, 2001, vol. 56, pp. 334 (with English Translation).
European Office Action dated Dec. 21, 2021 in European Patent Application No. 18788077.2, 5 pages.

* cited by examiner

DNA CHIP FOR DETECTING DENTAL CARIES BACTERIA

TECHNICAL FIELD

The present invention relates to a DNA chip for detecting dental caries bacteria, a probe to be carried by the chip, etc.

BACKGROUND ART

Periodontal disease and dental caries, the two major oral diseases, are bacterial infectious diseases involving multiple bacteria.

*Streptococcus mutans*, *Streptococcus sobrinus* and *Lactobacillus* are known as causative bacteria of dental caries. These causative bacteria are known to metabolize sugars to produce lactic acid, as a result of which oral environment becomes acidic and enamel decalcification occurs.

It has been reported that, in addition to the amount of existing causative bacteria, the ratio of *Streptococcus mutans* to the bacterial count of *Streptococci* existing in the oral cavity can be utilized as an index. Specifically, when the ratio of *Streptococcus mutans* to the bacterial count of *Streptococci* is high, dental caries is easily caused (for example, see Non-Patent Documents 1-3).

For a bacterial examination for dental caries, a kit is commercially available which examines by culturing *Streptococcus mutans* and *Lactobacillus*, and is utilized as one of the materials for diagnosis. The resulting cultures are visually observed to measure approximate colony counts and examination results are assessed.

However, since culture conditions of *Streptococcus mutans* differ from those of *Lactobacillus*, these must be cultured separately, and there was no technique for measuring them efficiently and simultaneously. Moreover, according to such a culture method, several days are required for the measurement, and there is a problem that it takes time to obtain assessment results.

PRIOR ART DOCUMENTS

Non-Patent Documents

Non-Patent Document 1: European Journal of Dentistry, January, 2007, Vol. 1, pp. 31-39
Non-Patent Document 2: Archives of Oral Biology, 1996, Vol. 41, pp. 167-73
Non-Patent Document 3: Japanese Journal of Bacteriology, 2001, Vol. 56, p. 334

SUMMARY OF THE INVENTION

Problems to be Solved by the Invention

Under such circumstances, it has been desired to develop, as a bacterial examination for dental caries, a means/method with which it is possible to quickly and efficiently detect causative bacteria of dental caries (a plurality of types of bacterial groups) and assess dental caries.

Means for Solving the Problems

The present invention was made in consideration of the above-described circumstances and provides a DNA chip, etc. described below.

[1] A DNA chip, which carries a probe (a) and at least one probe from among a probe (b) and a probe (c):

(a) a probe comprising a nucleic acid that hybridizes to 16S rRNA specific to each of one or more oral bacteria to be detected, wherein the probe is any of sequences (i) to (iii):
 (i) at least one sequence selected from nucleotide sequences represented by SEQ ID NOS: 2-7;
 (ii) a complementary sequence of a sequence of (i); and
 (iii) a sequence substantially identical to a sequence of (i) or (ii);
(b) a total amount indicator probe; and
(c) an absolute amount indicator probe of one type or a plurality of types.

[2] The DNA chip according to item [1], which is a fiber-type DNA chip.

[3] A probe set for detecting dental caries bacteria, which comprises a probe (a) and at least one probe from among a probe (b) and a probe (c):
(a) a probe comprising a nucleic acid that hybridizes to 16S rRNA specific to each of one or more oral bacteria to be detected, wherein the probe is any of sequences (i) to (iii):
 (i) at least one sequence selected from nucleotide sequences represented by SEQ ID NOS: 2-7;
 (ii) a complementary sequence of a sequence of (i); and
 (iii) a sequence substantially identical to a sequence of (i) or (ii);
(b) a total amount indicator probe; and
(c) an absolute amount indicator probe of one type or a plurality of types.

Effect of the Invention

According to the present invention, as a bacterial examination for dental caries, it is possible to provide a means/method with which it is possible to quickly and efficiently detect causative bacteria of dental caries (a plurality of types of bacterial groups) and assess dental caries.

Specifically, according to the present invention, the respective bacterial counts of *Lactobacilli*, *Streptococcus sobrinus* and *Streptococci* can be simultaneously calculated in a short time by using a DNA chip that carries probes corresponding to DNA sequences specific to the respective bacteria.

BEST MODE FOR CARRYING OUT THE INVENTION

Hereinafter, the present invention will be described in detail. The scope of the present invention is not limited to these descriptions and, besides the following examples, they can appropriately be modified and carried out without departing from the spirit of the present invention. This specification incorporates the entire content of the specification of Japanese Patent Application No. 2017-048654 (filed on Mar. 14, 2017) based on which the present application claims priority. Furthermore, all of the publications cited herein such as prior art documents and publications, patent publications and other patent documents are incorporated herein by reference.

As described above, the present invention relates to a DNA chip, which carries a probe (a) and at least one probe from among a probe (b) and a probe (c):
(a) a probe comprising a nucleic acid that hybridizes to 16S rRNA specific to each of one or more oral bacteria to be detected, wherein the probe is any of sequences (i) to (iii):
 (i) at least one sequence selected from nucleotide sequences represented by SEQ ID NOS: 2-7;
 (ii) a complementary sequence of a sequence of (i); and
}

(iii) a sequence substantially identical to a sequence of (i) or (ii);
(b) a total amount indicator probe; and
(c) an absolute amount indicator probe of one type or a plurality of types.

1. Probe (Probe Set)

The aforementioned probe (a) and the probe (b) and/or the probe (c) can be used as a probe set for detecting dental caries bacteria.

Hereinafter, each of these probes will be explained.

(1) Probe (a)

An oral bacterium to be detected is at least one, and preferably two or more of *Lactobacilli, Streptococcus sobrinus* and *Streptococci*.

The probe (a) can hybridize to a nucleotide sequence of a specific region in a nucleotide sequence of a nucleic acid derived from the oral bacterium. In this regard, the nucleic acid is preferably a chromosomal DNA.

Probes that can be used for the present invention are preferably designed from regions that can serve as specific nucleotide sequences for 16S rRNA gene in the chromosomal DNA of the above-described respective intraoral bacteria to be detected. In general, probe design requires, in addition to selection of specific regions, matching of melting temperatures (Tm) and minimization of formation of a secondary structure.

Meanwhile, the specificity of the probe may be such that it allows collective detection of bacteria belonging to the same genus based on the specificity at a genus level, or such that it allows detection based on the specificity at an individual species level, which can be suitably selected and determined according to the purpose of the bacteria detection. Regarding the length of the probe, for example, a sequence of 15 bases or longer, and preferably 17 bases or longer, and 100 bases or shorter, and preferably 80 bases or shorter can be employed.

Examples of the probe (a) are shown in Table 1 (SEQ ID NOS: 2-7).

TABLE 1

| SEQ ID NO | Probe sequence | Targeted bacteria |
|---|---|---|
| 1 | CGTATTACCGCGGCTGCTGGCAC | Total amount indicator probe |
| 2 | CAGTTTCCGATGCAGTTCC | Probe for *Lactobacilli* |
| 3 | GCCGTGACTTGCTGGTT | Probe for *Lactobacilli* |
| 4 | CTGTCCTCTTCTGCACT | Probe for *Lactobacilli* |
| 5 | TTTCCCAGTTTCCGATG | Probe for *Lactobacilli* |
| 6 | CCGTCACTGTGTAAGCTT | Probe for *Streptococcus sobrinus* |
| 7 | TTAGCCGTCCCTTTCTGG | Probe for *Streptococci* |
| 8 | CACACGTTCTTGACTTAC | Probe for *Streptococcus mutans* |
| 9 | CGTGCATTGTCGTGTAGGTTCGACCCTAAT | Probe for absolute amount indicator 1 |
| 10 | GCAGCTACGTTCATACCTACGCAAGGCATT | Probe for absolute amount indicator 2 |
| 11 | GAGGAGATACCGAATCGGTCGACGACATTT | Probe for absolute amount indicator 3 |
| 12 | TGTTGCGTGAAGGTCGTGAACGATTGGCAA | Probe for absolute amount indicator 4 |
| 13 | CCCCTACTGAGCAAACGTTGCACTAATGGA | Probe for absolute amount indicator 5 |
| 14 | AACAACGACCGAGTGCATAGTCACGTACGA | Probe for absolute amount indicator 6 |
| 15 | AGGAGCCCTAAGGTATTGGCGAGAAAAGTC | Probe for absolute amount indicator 7 |
| 16 | CTGAGTATCCGCATATCTTCCGAGGTTGCA | Probe for absolute amount indicator 8 |
| 17 | ACTTAGCTGACCGAAGGACCATAACGCTGT | Probe for absolute amount indicator 9 |
| 18 | TGGAAGGGATCCGTAGTCAACCGTTGACTT | Probe for absolute amount indicator 10 |
| 19 | CGGATCGACATACGACGCCTACAGAATGTT | Probe for absolute amount indicator 11 |
| 20 | TAAACGTCTAGGCGAGACTATGAGTGCTCC | Probe for absolute amount indicator 12 |
| 21 | CGTATGGATCGATCCGACGTACCACATTAG | Probe for absolute amount indicator 13 |
| 22 | ACTGCGTATGATCGACACGGCTAATCGTAG | Probe for absolute amount indicator 14 |
| 23 | CTATTCGACCAGCGATATCACTACGTAGGC | Probe for absolute amount indicator 15 |

The probe to be used for the present invention can be prepared, for example, through chemical synthesis employing a general oligonucleotide synthesis method. Such a probe can be designed, for example, by Probe Quest (registered trademark: manufactured by Dynacom). At the time of design thereof, it is required to set stringent conditions in consideration of conditions at the time of hybridization.

The term "stringent conditions" as used herein refers to conditions that are less likely to cause cross-hybridization induced by similar sequences, or that can dissociate any nucleic acids cross-hybridized with similar sequences. Specifically, it refers to the conditions for washing the DNA chip upon or after the hybridization reaction. For example, it is preferred that the salt concentration of a buffer is 48 to 780 mM, and that the temperature thereof is 37 to 80° C. As more stringent conditions, as conditions under which the probe sequences shown in Table 1 hybridize and other similar sequences do not hybridize, it is more preferred that the salt concentration is 97.5 to 390 mM and that the temperature is 45 to 60° C. Specific examples of conditions include those of 240 mM and 50° C.

Examples of DNA to be hybridized include a nucleotide sequence having preferably at least 60%, and more preferably at least 70%, at least 80%, at least 90%, at least 95%, at least 96%, at least 97%, at least 98%, or at least 99% homology (identity) to the nucleotide sequence of DNA of the probe.

The nucleotide sequence of the nucleic acid of the above-described intraoral bacterium to be detected in the present invention does not have to be the exact nucleotide sequence thereof, and for example, it may have partial mutations such as deletion, substitution and insertion in the nucleotide sequence.

Specific preferred examples of the probe to be used in the present invention include those consisting of a nucleotide sequence DNA of (i), (ii) or (iii) below:
(i) at least one sequence selected from nucleotide sequences represented by SEQ ID NOS: 2-7;
(ii) a complementary sequence of a sequence of (i); and
(iii) a sequence substantially identical to a sequence of (i) or (ii).

In this regard, the "sequence substantially identical" regarding the sequence of (iii) above is a nucleotide sequence which can hybridize to the sequence represented by any of SEQ ID NOS: 2-7 or the complementary sequence thereof under the aforementioned stringent conditions. More specific examples thereof include a nucleotide sequence having at least 60%, at least 70%, at least 80%, at least 90%, at least 95%, at least 96%, at least 97%, at least 98%, or at least 99% homology (identity) to the sequence represented by any of SEQ ID NOS: 2-7 or the complementary sequence thereof.

(2) Regarding Probe (b)

The total amount indicator probe is a probe intended to capture all of the bacteria in the specimen that were successfully amplified with specific primer pairs. With respect to bacteria detection, it is crucial to detect the total amount of bacteria from the viewpoint of how much the bacteria targeted for detection exist among the entire bacteria including bacteria not targeted for detection, and also from the viewpoint of how much level of bacteria are present in the specimen in the first place.

The bacteria not targeted for detection are understood as a sum (total) of bacteria whose presence and types are known but not targeted for detection, and bacteria whose presence and types are unknown.

For the detection of the total amount of bacteria, for example, the total amount of bacteria may be measured independently from the DNA chip, but convenience of handling/measurement would be enhanced by providing a probe that can serve as an index of the total amount of bacteria on the DNA chip. The probe to be used may be a nucleotide sequence that is common to various types of bacterial species among the nucleotide sequences amplified by the primer pairs. If no such sequence is found, a plurality of relatively common sequences may be designed to be subjected to comprehensive judgement, thereby providing a total amount indicator probe. The total amount indicator probe is preferably a probe that hybridizes to nucleic acids derived from the bacteria contained in the specimen, specifically, a probe that contains a nucleotide sequence commonly included by a plurality of types of bacteria targeted for detection among the nucleotide sequences amplified by the aforementioned specific primer pairs.

An example of the total amount indicator probe is shown in Table 1 (SEQ ID NO: 1).

(3) Regarding Probe (c)

An absolute amount indicator probe refers to a probe that hybridizes only to the nucleic acids of the absolute amount indicator.

As used herein, the absolute amount indicator refers to nucleic acids that are added to the specimen in a certain amount prior to amplification reaction and hybridization reaction. The absolute amount indicator is nucleic acids that ensure actual amplification reaction upon usual amplification reaction, and plays a role as a so-called positive control.

Therefore, when the DNA chip is provided with a probe specific to the absolute amount indicator, it can be confirmed from detection results thereof whether or not amplification reaction, hybridization and the like have been appropriately performed. Moreover, if one type of absolute amount indicator is set, the fluorescence intensity of said absolute amount indicator acquired from multiple DNA chips should be constant, and thus the fluorescence intensities of the absolute amount indicator may be compared to calculate correction coefficients if there are some variations in the amplification efficiency or the hybridization efficiency. The corrected fluorescence intensities can be used upon comparison among the multiple DNA chips.

Examples of the absolute amount indicator probe are shown in Table 1 (SEQ ID NOS: 9-23). Further, examples of nucleotide sequences which can serve as the absolute amount indicator (nucleotide sequences targeted for the detection using the absolute amount indicator probe) are shown in Table 2 (SEQ ID NOS: 24-38).

TABLE 2

| SEQ ID NO | Name | Sequence (5' to 3') |
|---|---|---|
| 24 | Absolute amount indicator 1 | GTGAGAAGCCTACACAAACGTAACGTCAGGGCTAAGACAAACGCTAACGGTACACCCTAGATGGGAGCTTGTAGCTAGATCGCTAAGT CCTACCGACATGTAGGCATACTCACGAAGGCAATTCCCTGAAACGCTCGTCTTATCCCGAACTTGGCATCTGCTGATACGTCAGGTTG AACGCGTACATTTACCTGTCATGCGTGAATGGTAAGGGTCGTATTAGGGTCGAACCTACACGACAATGCACGTCGAAGCGGTTGCTAA TGCACATTGGCTAAGGCCCACGGAACACGAATCACGTGAGATCACTTACTATTCGAGGGAACTACTATACGCACCGGGACATGCAAGT |

TABLE 2-continued

| SEQ ID NO | Name | Sequence (5' to 3') |
|---|---|---|
| | | AGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 25 | Absolute amount indicator 2 | GTGAGAACCCTACACAAACGTAACGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGGTAGCCGATTGAACTAATGCCTTGCGTAGGTATGAACGTAGCTGCTAGTCGAGGCCTTGTATGCACATTGGCTAAGGCCCACGGAACACGAATCACGTGAGATCACTTACTATTCGACGGAACTACTATACGCACCGGGACATGCAAGTAGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 26 | Absolute amount indicator 3 | GTGAGAAGCCTACACAAACGTAACGTCAGGGCTAAGACAAACGGTAACGGTACACCCTAGATGGGAGCTTGTAGCTAGATCGCTAAGTCCTACCGACATGTAGGCATACTCACGAAGGCAATTCCCTGAAAGAAATCCGTGTTATCCCGAACTTGGCATCTGCTGATACGTCAGGTTGAACGCGTACATTTACCTGTCATGCGTGTGCTCGATAGATAGGAAATGTCGTCGACCGATTCGGTATCTGGTCTGGGAGGGAAGAGAAATGGAGATTGGCTAAGGCCCACGGAACACGAATCACGTGAGATCACTTACTATTCGACGGAACTACTATACGCACCGGGACATGCAAGTAGCGTCCCACAAGCATAAGGAACTCTATACTCGCCATCTACGCAGCTACAGGGGATAGACGTATGAGCCGTTACGAAGTAAAGCCGAGATAGAGCGGTGTTTAGAGA |
| 27 | Absolute amount indicator 4 | GTGAGAAGCCTACACAAACGTAACGTCAGGGCTAAGAGAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGTGCTACGCTTTACGCTTGCCAATCGTTCACGACCTTCACGCAACACTTGATCGAACCGAAATGCACATTGGCTAAGGCCCACGGAAGCGAATCACGTGAGATCACTTACTATTCGACGGAACTACTATAGGCACCGGGACATGCAAGTAGCGTCCCACAAGCATAAGGAACTCTATACTCGCCATCTACGCAGCTAGAGGGGATACACGTATGAGCGGTTACGAAGTAAAGCCGAGATAGAGCGGTCTTTAGAGA |
| 28 | Absolute amount indicator 5 | GTGAGAAGCCTACACAAACGTAACGTCAGGGCTAAGAGAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGACAACAGACGGTACGTCCATTAGTGCAACGTTTGCTCAGTAGGGGGTCTAAGCGTCACTTATCCACATTGGCTAAGGCCCACGGAACACGAATCACGTGAGATCACTTACTATTCGACGGAACTACTATACGCACCGGGACATGCAAGTACCGTCCCACAAGCATAAGGAACTCTATACTCGCCATCTACGCAGCTACAGGGATACACGTATGAGCGGTTACGAAGTAAAGCCGAGATAGAGCGGTCTTTAGAGA |
| 29 | Absolute amount indicator 6 | GTGAGAAGCCTACACAAACGTAACGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCACGTTGAACGCGTACATTTACCTGTCATGCGTGGGACAGTTTTCTTCTACGTGACTATGCACTCGGTCGTTGTTGGAATACCGGTCGTAATGCACATTGGCTAAGGCCGACGGAACACGAATCACGTCAGATCACTTACTATTCGACGGAACTACTATACGGCACCGGGACATGCAAGTAGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 30 | Absolute amount indicator 7 | GTGAGAAGCCTACACAAACGTAACGTCAGGGCTAAGAGAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGAACGCAATACGGTGGACTTTTCTCGCCAATACCTTAGGGCTCCTGTGTACCTAAGCGAAATGCACATTGGCTAAGGCCCACGGAACACGAATCACGTGAGATCACTTACTATTCGAGGGAACTACTATAGGCACCGGGACATGCAAGTAGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 31 | Absolute amount indicator 8 | GTGAGAAGCCTACACAAACGTAACGTGAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGGGATGACGGATAAGTTGCAACCTCGGAAGATATGCGGATACTCAGACGTGATATGCGCAGATGCACATTGGCTAAGGCCCACGGAACACGAATCACGTGAGATCACTTACTATTCGACGGAACTACTATACGCACCGGGACATGCAAGTAGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 32 | Absolute amount indicator 9 | GTGAGAACCCTACACAAACGTAACGTCAGGGCTAAGACAAACGCTAACGGTACACCCTAGATGGGAGGTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGGGTGTACATCGGATGACAGCGTTATGGTCCTTCGGTCAGCTAAGTAAGTCCGTTTTCCACATGCACATTGGCTAAGGCCCACGGAACACGAATCACGTGAGATCACTTACTATTCGACGGAACTACTATACGCACCGGGACATGCAAGTAGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 33 | Absolute amount indicator 10 | GTGAGAAGCCTACACAAACGTAACGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACGTGTCATGCGTGTTCAGTCAACCGGAGAAGTCAACGGTTGACTACGGATCCCTTCCATGTAGAGCTCTCACAATGCACATTGGCTAAGGCCCACGGAACACGAATCACGTGAGATCACTTACTATTCGACGGAACTACTATACGCACCGGGACATGCAAGTAGCGTCCCACAAGCATAAGGAACTCTATACTCGCCATCTACGCAGCTAGAGGGGATACACGTATGAGCGGTTAGGAAGTAAAGCCGAGATAGAGCGGTCTTTAGAGA |
| 34 | Absolute amount indicator 11 | GTGAGAAGCCTACACAAACGTAACGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACGTGTCATGCGTGGCGATTGTCGCGTTAAACATTCTGTAGGCGTCGTATGTCGATCGGGACTTGCTTCATAATGCACATTGGCTAAGGCCCACGGAAGACGAATCACGTGAGATCACTTACTATTCGACGGAACTACTATACGCACCGGGACATGCAAGTAGCGTCCCACAAGCATAAGGAACTCTATACTCGCCATCTACGCAGCTACAGGGGATACACGTATGAGCGGTTACGAAGTAAAGCCGAGATAGAGCGGTCTTTAGAGA |
| 35 | Absolute amount indicator 12 | GTGAGAAGCCTACACAAACGTAACGTCAGGGCTAAGAGAAACGCTAACGGTACACCCTAGATGGGAGCTTGTAGCTAGATCGCTAAGTCCTACCGACATGTAGGCATACTCAGGAAGGCAATTCCCTGAAAGCCTCGTCTTATCCCGAAGTTGGCATCTGCTGATACGTCAGGTTGAACGCGTACATTTACCTGTCATGCGTGTCGTGTCGTGAGAGGAGCACTCATAGTCTCGCCTAGACGTTTATGACGAGATATCACGATGCACATTGGCTAAGGCCCACGGAACACGAATCACGTGAGATCACTTACTATTCGACGGAACTACTATACGCACCGGGACATGCAAGT |

TABLE 2-continued

| SEQ ID NO | Name | Sequence (5' to 3') |
|---|---|---|
|  |  | AGCGTCCCACAAGCATAAGGAACTCTATACTCGCCATCTACGCAGGTACAGGGGATACACGTATGAGCGGTTACGAAGTAAAGCCGAGATAGAGCGGTCTTTAGAGA |
| 36 | Absolute amount indicator 13 | GTGAGAAGCCTACACAAACGTAAGGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCGTCGTCTTATCCCGAACTTGGCATCTGCTGATACGTCAGGTTGAACGCGTACATTTACCTGTCATGCGTGGTAGCGTGTAACGCACTAATGTGGTACGTCGGATCGATCCATACGCAACTTTGTACCGAGATGCACATTGGCTAAGGCCCACGGAAGACGAATCACGTGAGATCACTTACTATTCGACGGAACTACTATACGCACCGGGACATGCAAGTAGCGTCCCACAAGCATAAGCAACTCTATACTCGCCATCTACGCAGGTACAGGGGATACACGTATGAGCGGTTACGAAGTAAAGCCGAGATAGAGCGGTCTTTAGAGA |
| 37 | Absolute amount indicator 14 | GTGAGAAGCCTACACAAACGTAACGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGAGCAACCATCTTGAGCTACGATTAGCCGTGTCGATCATACGCAGTCCGAGGCATTACTGAATGCACATTGGCTAAGGCCCACGGAACACGAATCACGTGAGATCACTTACTATTCGACGGAACTACTATACGCACCGGGACATGCAAGTAGCGTCCCAGAAGCATAAGCAACTCTATACTCGCCATCTACGCAGCTAGAGGGGATACACGTATGAGCGGTTACGAAGTAAAGCCGAGATAGAGCGGTCTTTAGAGA |
| 38 | Absolute amount indicator 15 | GTGAGAAGCCTACAGAAACGTAACGTCAGGGCTAAGACAAACGCTAACGGTACACCCTAGATGGGAGCTTGTAGCTAGATCGCTAAGTCCTACCGACATGTAGGCATACTCACGAAGGCAATTCCCTGAAAGCCTCGTCTTATCCCGAACTTGGCATCTGCTGATACGTCAGGTTGAACGCGTACATTTACCTGTCATGCGTGGGCCTTCTCCGAATAGCCTACGTAGTGATATCGCTGGTCGAATAGGCGGATTGCTCATAAATGCACATTGGCTAAGGCCCACGGAACACCAATCACGTGAGATCACTTACTATTCGACGGAACTACTATACGCAGCGGGACATGCAAGTAGCGTCCCACAAGCATAAGGAACTCTATACTCGCCATCTACGCAGCTAGAGGGGATACACGTATGAGCGGTTACGAAGTAAAGCCGAGATAGAGCGGTCTTTAGAGA |

The absolute amount indicator may be a nucleic acid standard substance for quantitative analysis, which was developed by the National Institute of Advanced Industrial Science and Technology (AIST), or it may be newly designed. When the absolute amount indicator is to be designed, for example, the RANDBETWEEN function of software "EXCEL" (from MICROSOFT) may be used, which can randomly return X number (X is a given number) of integers of 1 to 4. The resulting random integers may be linked in a row to give a X-digit number consisting only of 1 to 4 so as to obtain a large number of sequences having X bases of random ATGC by converting 1 to A, 2 to T, 3 to C and 4 to G.

From these sequences, only sequences that have the sum of G and T equal to the sum of A and T are picked out. The picked sequences are subjected to Blast search against database such as GenBank at NCBI so as to select less homologous sequences among organism-derived nucleic acids. Primer sequences are allowed to flank both ends of the sequence, thereby designing a sequence. Moreover, the designed sequence may suitably be linked for extension or partially removed for shortening.

In order to keep the reaction efficiency upon amplification reaction as constant as possible, the difference between the amplified base length of the bacterium targeted for detection and the amplified base length of the absolute amount indicator is preferably made small. For example, if the amplified product of the bacterium targeted for detection is about 500 bp, the amplified product of the absolute amount indicator is preferably made to be about 300 bp to 1000 bp.

On the other hand, if the amplified chain length is to be confirmed by electrophoresis or the like after the amplification, the amplified product of the absolute amount indicator is designed to have a length that differs from the length of that of the bacterium targeted for detection so that the absolute amount indicator-derived amplified product can be detected at a location separated from the band for the bacterium targeted for detection, thereby confirming success/failure of the amplification reaction prior to hybridization.

If the absolute amount indicator is added prior to amplification reaction, it should be nucleic acids that can be amplified with a specific primer pair, in other words, it should possess a nucleotide sequence complementary to the primer pair, and it should possess a nucleotide sequence that is not possessed by any of the bacteria targeted for detection or the bacteria not targeted for detection in order to be detected through hybridization.

A specific primer means that the sequence targeted for amplification can be limited, where the primer pair is not necessary a single pair. If necessary, a multiplex technique that uses two or more primer pairs may also be applied. Examples of the primer pairs are shown in Table 3. A primer pair for absolute amount indicator (SEQ ID NOS: 39 and 40) and a primer pair for bacterial amplification (SEQ ID NOS: 41 and 42) may be used.

TABLE 3

| SEQ ID NO | Name of primer | Sequence (5' to 3') |
|---|---|---|
| 39 | Forward primer (for amplification of absolute amount indicator) | GAGAAGCCTACACAAACGT AACGTC |
| 40 | Reverse primer (for amplification of absolute amount indicator) | CTCTAAAGACCGCTCTATCT CGG |
| 41 | Forward primer (for bacterial amplification) | TACGGGAGGCAGCAG |
| 42 | Reverse primer (for bacterial amplification) | CRGGGTATCTAATCCYGTT |

2. DNA Chip

The DNA chip of the present invention has a plurality of various probes described in Item 1 above arranged (mounted) on a substrate that serves as a support.

The substrate that serves as a support may be in any form of a flat plate (glass plate, resin plate, silicon plate, etc.), a stick, beads or the like. When a flat plate is used as the support, predetermined probes can be fixed thereon by types at predetermined intervals (spotting method, etc.; see Science 270, 467-470 (1995), etc.). Alternatively, predetermined probes can sequentially be synthesized thereon by types at specified positions (photolithography method, etc.; see Science 251, 767-773 (1991), etc.). Another preferable form of the support may be, for example, one that uses hollow fibers. When hollow fibers are used as a support, a preferable exemplary DNA chip (hereinafter referred to as a "fiber-type DNA chip") can be obtained by fixing predetermined probes in respective hollow fibers by types, bundling and fixing all of the hollow fibers, and then repeatedly cutting the fibers with respect to the longitudinal direction of the fibers. This DNA chip may also be referred to as a DNA chip that has nucleic acids fixed in through holes of a substrate, which is also referred to as a so-called "through-hole-type DNA chip" (see Japanese Patent No. 3510882, etc.).

The method for fixing probes onto a support is not limited, and any binding mode can be employed. Moreover, fixing is not limited to direct fixing onto the support. For example, a support may be pre-coated with a polymer such as polylysine so that probes may be fixed onto the treated support. Furthermore, when a tubular body such as hollow fibers is used as a support, the tubular body may be made to retain a gel-like substance so that probes can be fixed to the gel-like substance.

Hereinafter, a fiber-type DNA chip, one form of DNA chips, will be described in detail. The fiber-type DNA chip can be prepared, for example, through Steps (i)-(iv) below.
  (i) Step of three-dimensionally arranging a plurality of hollow fibers such that the hollow fibers are oriented in the same longitudinal direction to produce an arranged body.
  (ii) Step of embedding the arranged body to produce a block body.
  (iii) Step of introducing a gel-precursor polymerizable solution containing a probe into a hollow of each hollow fiber of the block body to allow polymerization reaction, thereby making the hollow to retain the gel-like substance containing the probe.
  (iv) Step of cutting the hollow fibers in a direction intersecting with the longitudinal direction thereof to slice the block body.

Examples of the material to be used as the hollow fiber preferably include, but are not limited to, a material described in Japanese Laid-Open Patent Publication No. 2004-163211.

The hollow fibers are three-dimensionally arranged such that their lengths are equal in the longitudinal direction (Step (i)). The method employed for the arrangement may be, for example, a method in which a plurality of hollow fibers are arranged in parallel at predetermined intervals on a sheet-like material such as an adhesive sheet to form a sheet, which is thereafter wound up in spiral (see Japanese Laid-Open Patent Publication No. H11-108928), or a method in which two porous plates provided with a plurality of pores at predetermined intervals are layered such that the pores meet each other, where hollow fibers are passed through the pores and then the two porous plates are temporary fixed at a distance and a curable resin material is charged and cured around the hollow fibers between the two porous plates (see Japanese Laid-Open Patent Publication No. 2001-133453).

The produced arranged body is embedded so that the arrangement is not disordered (Step (ii)). The method of embedment may preferably be a method in which a polyurethane resin, an epoxy resin or the like is poured into the gap between the fibers, a method in which the fibers are adhered to each other by heat welding, or a method likewise.

The hollow of each hollow fiber of the embedded arranged body is filled with a gel-precursor polymerizable solution (gel-forming solution) containing the probe to allow polymerization reaction in the hollow (Step (iii)). As a result, the hollow of each hollow fiber can retain the gel-like substance having the probe fixed thereto.

The gel-precursor polymerizable solution refers to a solution containing a reactive substance such as a gel-forming polymerizable monomer, where said monomer or the like can be polymerized/crosslinked so that the solution becomes a gel-like substance. Examples of such monomer include acrylamide, dimethylacrylamide, vinylpyrrolidone and methylene-bis-acrylamide. In this case, the solution may contain a polymerization initiator and the like.

After fixing the probes in the hollow fibers, the block body is cut into slices in a direction intersecting with (preferably perpendicular to) the longitudinal direction of the hollow fibers (Step (iv)). The resulting slice can be used as a DNA chip. The thickness of this DNA chip is preferably about 0.01 mm to 1 mm. The block body can be cut, for example, with a microtome, a laser or the like.

Preferable examples of the above-described fiber-type DNA chip include a DNA chip (Genopal™) manufactured by Mitsubishi Rayon Co., Ltd.

In the fiber-type DNA chip, the probes are three-dimensionally arranged in the gel as described above so as to maintain a three-dimensional structure. Accordingly, the detection efficiency is enhanced as compared to a flat DNA chip that has probes bound onto a coated surface of a glass slide, and thus a highly sensitive and highly reproducible examination can be realized.

The number of types of probes arranged on the DNA chip is 500 types or less, preferably 250 types or less and more preferably 100 types or less per DNA chip. By limiting the number (types) of the arranged probes to some extent, the intraoral bacteria of interest can be detected with higher sensitivity. The types of the probes are distinguished by the nucleotide sequences. Therefore, usually, even probes that are derived from the same gene are specified as different types of probes even if just a single difference exists between the nucleotide sequences.

3. Method for Measuring the Number of Intraoral Bacteria

The method for measuring the number of intraoral bacteria is, for example, a method comprising the following steps.
  (I) Step of extracting nucleic acids of bacteria contained in a specimen, which is an intraoral sample collected.
  (II) Step of bringing the extracted nucleic acids into contact with the DNA chip of the present invention (or the probe of the present invention) described above.
  (III) Step of calculating the number of bacteria based on the fluorescence intensity obtained from the DNA chip (or probe) after the contact.

Hereinafter, the steps of the measurement method will be described one by one in detail.

(1) Regarding Step (I)

In this step, an intraoral sample (intraoral bacteria (bacterial group)) collected is used as a specimen, where the nucleic acids of the bacteria contained in the specimen are extracted. The specimen can be collected, for example, from a desired subject human or organism. The type of the intraoral sample collected is not particularly limited. For example, saliva, plaque (subgingival plaque, supragingival plaque), tongue fur, mousewash or the like may be used.

In the case where saliva is used as the intraoral sample, the method for collecting saliva is not particularly limited, and examples thereof include a method in which saliva is directly flowed into a container, and a method in which saliva is impregnated into a cotton swab or another paper-like product. A subject human may chew gum before the collection of saliva so that saliva can be easily collected.

When the collected sample is transported, it is preferred to employ a transport method in which the collected sample is put into an airtight container and frozen, or a transport method in which a cotton swab with a case is used, wherein the sample is collected using the cotton swab, which is put into the case.

The amount of saliva to be collected is not particularly limited and can be suitably selected depending on the method for detecting DNAs of bacteria present in the intraoral sample. For example, in the case where the gene DNA in a sample is detected using a DNA chip, the amount of saliva of a subject human is preferably 0.1 mL or more, and more preferably 0.5 mL or more.

Without limitation, the nucleic acids obtained from the specimen may be allowed to make direct contact with the DNA chip or the like, or a nucleotide sequence region desired may be amplified by PCR or the like so as to allow the amplified fragments thereof to make contact with the DNA chip or the like. Specifically, for example, the site desired to be amplified is preferably ribosome RNA (16S rRNA) gene in chromosomal DNAs of the intraoral bacteria. PCR primers that can be used for amplification of this region may preferably be, for example, SEQ ID NOS: 41 and 42 shown in Table 3. The amplification of the nucleic acids by the PCR method can be carried out according to a common method.

The extracted nucleic acids and the amplified fragments thereof in this step may suitably be labeled so as to be used in the detection process following hybridization. Specifically, a method in which the terminal of the PCR primer is labeled with a reporter dye, a method in which a reactive nucleotide analog is incorporated upon reverse transcription reaction, a method in which biotin-labeled nucleotides are incorporated, and the like may be contemplated. Furthermore, labeling can be carried out through reaction with a fluorescently labeled reagent after preparation. As the fluorescent reagent, for example, various kinds of reporter dyes (e.g., Cy5, Cy3, VIC, FAM, HEX, TET, fluorescein, FITC, TAMRA, Texas red, Yakima Yellow, etc.) can be used.

(2) Regarding Step (II)

In this step, the nucleic acids or the amplified fragments thereof obtained in Step (I) are allowed to make contact with the probes or the DNA chip to be used in the present invention. Specifically, a hybridization solution containing said nucleic acids or the like is prepared so as to allow the nucleic acids or the like in said solution to bind (hybridize) to the probe mounted on the DNA chip. The hybridization solution can suitably be prepared using a buffer such as SDS or SSC according to a common method.

The hybridization reaction can be carried out by suitably setting reaction conditions (type, pH, temperature and the like of the buffer) such that the nucleic acids or the like in the hybridization solution can hybridize with the probe mounted on the DNA chip under stringent conditions.

After washing, the detected intensity of each spot is measured with a device that can detect the label of the nucleic acids or the like bound to the probe. For example, if the above-described nucleic acids or the like are fluorescently labeled, a fluorescence detector such as CRBIO (from Hitachi Software Engineering), arrayWoRx (from GE Healthcare), Affymetrix 428 Array Scanner (from Affymetrix), GenePix (from Axon Instruments), ScanArray (from PerkinElmer) or Genopal Reader (from Mitsubishi Rayon) can be used to measure the fluorescence intensity. In the case where the device is a fluorescence scanner, scanning can be performed by suitably adjusting, for example, the laser output and sensitivity of the detection section, whereas in the case where the device is a CCD camera type scanner, scanning can be performed by suitably adjusting the exposure time. A quantitative method based on the scan results can be performed with a quantification software. The quantification software is not particularly limited, and the average value, the median or the like of the fluorescence intensity of the spot can be used for quantification. Furthermore, considering the dimensional accuracy of the spot area of the DNA fragment and the like, adjustment is preferably performed upon quantification, for example, using the fluorescence intensity of the spot having no probe as background.

(3) Regarding Step (III)

In this step, the number of bacteria of the bacterial species targeted for detection is calculated based on the fluorescence intensity obtained from the DNA chip (or probes) through the procedures of Step (I) and Step (II). For example, there is a method in which the SN ratio is expressed based on the fluorescence intensity of the probe for detecting the bacterium targeted for detection and the fluorescence intensity of the background. Alternatively, it may be preferable to conduct detections for each bacterium under a plurality of conditions by varying the bacterial chromosomal DNA concentration so as to acquire a conversion factor (standard curve) for each bacterium in advance for calculating the chromosomal DNA concentration based on the fluorescence intensity obtained under each concentration condition, by which chromosomal DNA concentrations can be calculated from fluorescence intensities obtained under the respective conditions.

In either case, a correction coefficient may be calculated for each DNA chip so that fluorescence intensities of an absolute amount indicator probe acquired by detection of a plurality of DNA chips will be constant. Accordingly, comparison can be made among the DNA chips by taking the correction coefficient into account for a fluorescence intensity of a bacterium targeted for detection from each DNA chip.

EXAMPLES

Hereinafter, the present invention will be described more specifically by way of examples, although the present invention should not be limited thereto.

Example 1

Designing DNA Probes for Detecting Bacteria

In order to design DNA probes for detecting bacteria, attention was focused on V3 and V4 as the variable regions of 16S rRNA. Among the V3 and V4 regions, sequences specific to the respective bacteria were selected to design and prepare nucleotide sequences represented by SEQ ID NOS: 2-7.

Example 2

Assessment of DNA Probe for Bacteria Detection

Measurement Target 100 pg of genomic DNA derived from the respective bacteria purchased from ATCC was used as a specimen to be measured to evaluate performance of the bacteria-specific probes designed/prepared in Example 1.

PCR

PCR was conducted with the following reaction liquid composition and reaction conditions to amplify the sequences of the regions of 16S rRNA targeted for detection of the bacteria-derived genomic DNA. Amplification reaction was conducted with ProFlex (from Applied Biosystems) using Premix Ex Taq™ Hot Start Version (from Takara) as a PCR kit. Primer conditions shown below were used. The 5'-terminal of the forward primer was labeled with Cy5 to label the terminal of the amplified product.

```
<Primer sequences>
Forward primer:
                                        (SEQ ID NO: 41)
5'Cy5-TACGGGAGGCAGCAG-3'

Reverse primer:
                                        (SEQ ID NO: 42)
5'-CRGGGTATCTAATCCYGTT-3'
```

Reaction Liquid Composition

| | |
|---|---|
| 2 x Premix Ex Taq (registered trademark) Hot Start Version | 10 μL |
| 4 μM Forward primer (for bacterial amplification) (SEQ ID NO: 41) | 1 μL |
| 4 μM Reverse primer (for bacterial amplification) (SEQ ID NO: 42) | 1 μL |
| 4 μM Forward primer (for amplification of absolute amount indicator) (SEQ ID NO: 39) | 1 μL |
| 4 μM Reverse primer (for amplification of absolute amount indicator) (SEQ ID NO: 40) | 1 μL |
| 20 pg of specimen-derived DNA | 5 μL |
| 1 pg of absolute amount indicator | 1 μL |
| Total | 20 μL |

Reaction Conditions

After heating at 95° C. for a minute, a total of 40 cycles of "dissociation at 98° C. (10 sec), annealing at 50° C. (30 sec) and synthesis at 72° C. (20 sec)", and cooling at 4° C. were conducted to obtain an amplified product.

DNA Chip: Production of DNA Chip for Detecting Intraoral Bacteria

A through-hole-type DNA chip was produced in the same manner as the method described in Example 1 of Japanese Laid-Open Patent Publication No. 2007-74950 (method for detecting methylated DNA and/or unmethylated DNA).

In this regard, the mounted probes were probes having the sequence information represented by SEQ ID NOS: 1-7 and 23 in Table 1.

Hybridization with DNA Chip

The following solutions were mixed to prepare a hybridization solution.

| | |
|---|---|
| Amplified DNA product obtained by PCR | 20 μL |
| 1M Tris-HCl | 48 μL |
| 1M NaCl | 48 μL |
| 0.5% Tween 20 | 20 μL |
| Water | 64 μL |
| Total | 200 μL |

Using an automatic hybridization/washing machine (model: ARE-200, Mitsubishi Rayon), 200 μL of the hybridization solution was allowed to make contact with the above-described DNA chip and allowed to hybridize therewith at 50° C. for 16 hours.

Following hybridization, the DNA chip was washed under the following conditions. Washing with 1000 μL of a 0.24M Tris-HCl/0.24M NaCl/0.05% Tween-20 solution for 220 seconds was repeated for 12 times, followed by washing with 1000 μL of 0.24M Tris-HCl/0.24M NaCl for 220 seconds repeated for 4 times.

After washing was finished, each chip was transferred into a 0.24M Tris-HCl/0.24M NaCl mixed solution at room temperature.

Detection

Following washing, the fluorescence intensity of each spot on the DNA chip was measured under the following conditions using Genopal Reader (model: GR-S1, Mitsubishi Rayon).

Detection Conditions

Center excitation wavelength: 633 nm

Exposure time: 0.1, 1, 4 and 40 seconds

Results

The background value (median of fluorescence intensities of spots having no probe mounted) was subtracted from the fluorescence intensity of the spot on which a probe for detecting a targeted bacterium was mounted to calculate the fluorescence intensity resulting from hybridization. As a result, as shown in Table 4, the fluorescence intensity of the total amount indicator probe that plays a role as a positive control was recognized in every bacterium-derived genomic DNA, and validity of the reaction was confirmed. Moreover, in each bacterium probe of the present invention, the fluorescence intensity was obtained only with respect to a bacterium of interest. According to the above-described results, it was shown that each of the probes of the present invention has high specificity.

TABLE 4

| | SEQ ID NO | Bacterium targeted by probe | L. acidphilus | L. rhamnosus | L. casei | L. salivarius | S. gordonii | S. mutans | S. intermedius | S. sobrinus | S. sanguinis | S. oralis | S. salivarius |
|---|---|---|---|---|---|---|---|---|---|---|---|---|---|
| Probe | 1 | Total Bacteria | 455205 | 516315 | 623778 | 696486 | 1756274 | 2197310 | 862518 | 938833 | 710164 | 738047 | 700896 |
| | 2 | Lactobacilli | 225143 | 64119 | 1648 | 0 | 0 | 0 | 0 | 0 | 0 | 0 | 0 |
| | 3 | Lactobacilli | 107582 | 0 | 0 | 1107138 | 0 | 0 | 0 | 0 | 0 | 0 | 0 |
| | 4 | Lactobacilli | 2659 | 29370 | 82866 | 3939 | 0 | 0 | 0 | 0 | 0 | 0 | 0 |
| | 5 | Lactobacilli | 323 | 36137 | 38194 | 561 | 0 | 0 | 0 | 0 | 0 | 0 | 0 |
| | 6 | S. sobrinus | 0 | 0 | 0 | 0 | 0 | 0 | 0 | 64977 | 0 | 0 | 0 |
| | 7 | Streptococci | 0 | 0 | 0 | 0 | 1829694 | 2146718 | 925017 | 612531 | 765858 | 849396 | 722606 |
| | 23 | control DNA | 272015 | 342104 | 267196 | 234432 | 119620 | 116911 | 196388 | 215415 | 259807 | 263777 | 258638 |

Example 3

Measurement of the Number of Bacteria in Saliva Specimen

Preparation of DNA

With the cooperation of five healthy adults, a saliva assessment test was conducted. The saliva of the five adults, i.e., Subjects A, B, C, D and E, were assessed.

Saliva was collected by placing γ-collection swab RI (Eiken Chemical) in the mouse for a minute. The γ-collection swab RI was immersed in water in a tube and left at room temperature for 5 minutes to elute the bacterial components. Thereafter, the γ-collection swab RI was removed and the tube was placed in a centrifuge. DNAs were extracted from the resulting pellets using DNeasy Blood & Tissue Kit (QIAGEN).

DNA Analysis

PCR and detection for DNA analysis were carried out under the same conditions as those in Example 2. In this regard, the probes mounted on the DNA chip were probes having the sequence information represented by SEQ ID NOS: 1, 4, 6, 7, 8 and 23 in Table 1.

Results

The background value (median of fluorescence intensities of spots having no probe mounted) was subtracted from the fluorescence intensity of the spot on which a probe for detecting a targeted bacterium was mounted to calculate the fluorescence intensity resulting from hybridization.

In addition, like Example 2, a plurality of bacterial DNAs whose concentrations were already known were assessed to make a standard curve and the fluorescence intensity was converted to the bacterial count in 1 ml of saliva. As a result, as shown in Table 5, the amount of each of existing five types of bacteria of interest and the ratio of *Streptococcus mutans* to the bacterial count of *Streptococci* were successfully calculated.

TABLE 5

| | | Subject A | Subject B | Subject C | Subject D | Subject E |
|---|---|---|---|---|---|---|
| Bacterial count in 1 ml of saliva | Total bacteria | 92000000 | 10000000 | 9900000 | 1700000 | 370000000 |
| | Lactobacilli | 290000 | 40000 | 1300000 | 370000 | 34000 |
| | S. sobrinus | 25000 | 170000 | 101000 | 0 | 0 |
| | Streptococci | 42000000 | 6400000 | 5400000 | 780000 | 150000000 |
| | S. mutans | 0 | 81000 | 64000 | 0 | 0 |
| Ratio of S. mutans to Streptococci | | 0.0% | 1.3% | 1.2% | 0.0% | 0.0% |

According to the above-described results, many items, i.e., the amount of each of existing dental caries-related bacteria, *Streptococcus mutans, Streptococcus sobrinus, Lactobacilli* and *Streptococci*, and the ratio of *Streptococcus mutans* to the bacterial count of *Streptococci* in the oral cavity were successfully calculated simultaneously in a short time.

INDUSTRIAL APPLICABILITY

According to the present invention, as a bacterial examination for dental caries, it is possible to provide a means/method with which it is possible to quickly and efficiently detect causative bacteria of dental caries (a plurality of types of bacterial groups) and assess dental caries.

Specifically, according to the present invention, the respective bacterial counts of *Lactobacilli, Streptococcus sobrinus* and *Streptococci* can be simultaneously calculated in a short time by using a DNA chip that carries probes corresponding to DNA sequences specific to the respective bacteria.

Sequence Listing Free Text

SEQ ID NOS: 1-42: synthetic DNAs

The invention claimed is:

1. A DNA chip, comprising:
  (a) two or more probes each comprising a nucleic acid that hybridizes to 16S rRNA specific to each of one or more oral bacteria to be detected, wherein the two or more probes comprise:
  at least one first probe having a first nucleotide sequence selected from SEQ ID NOS: 6 and 7, the complementary sequence of the first nucleotide sequence, or a sequence having at least 60% homology to the first nucleotide sequence or the complementary sequence of the first nucleotide sequence, and
  at least one second probe having a second nucleotide sequence selected from SEQ ID NOS: 2-5, the complementary sequence of the second nucleotide sequence, or a sequence having at least 60% homology to the second nucleotide sequence or the complementary sequence of the second nucleotide sequence;
  (b) a total amount indicator probe; and
  (c) an absolute amount indicator probe,
  wherein the DNA chip is a fiber-type DNA chip.

2. The chip of claim 1, wherein the first probe has the nucleotide sequence of SEQ ID NO: 6 or 7, and the second probe has the nucleotide sequence of SEQ ID NO: 4.

3. The chip of claim 1, wherein the first probe has the nucleotide sequence of SEQ ID NO: 6 or 7, and the second probe has the nucleotide sequence of SEQ ID NO: 2, 3, 4, or 5.

4. The chip of claim 1, wherein the probes (a) further comprise a third probe having a third nucleotide sequence of SEQ ID NO: 8, the complementary sequence of the third nucleotide sequence, or a sequence having at least 60% homology to the third nucleotide sequence or the complementary sequence of the third nucleotide sequence.

5. The chip of claim 1, wherein the probes (a) comprise two first probes, one having the nucleotide sequence of SEQ ID NO: 6 and the other having the nucleotide sequence of SEQ ID NO: 7.

6. The chip of claim 1, wherein the probe (b) has the nucleotide sequence of SEQ ID NO: 1, and the probe (c) has the nucleotide sequence of SEQ ID NO: 23.

7. The chip of claim 1, wherein the first probe has a sequence having at least 70% homology to the first nucleotide sequence selected from SEQ ID NOS: 6 and 7, and the second probe has a sequence having at least 70% homology to the second nucleotide sequence selected from SEQ ID NOS: 2-5.

8. The chip of claim 1, wherein the first probe has a sequence having at least 80% homology to the first nucleotide sequence selected from SEQ ID NOS: 6 and 7, and the second probe has a sequence having at least 80% homology to the second nucleotide sequence selected from SEQ ID NOS: 2-5.

9. The chip of claim 1, wherein the first probe has a sequence having at least 95% homology to the first nucleotide sequence selected from SEQ ID NOS: 6 and 7, and the second probe has a sequence having at least 95% homology to the second nucleotide sequence selected from SEQ ID NOS: 2-5.

10. The chip of claim 1, wherein probes in the chip consist of the probes (a), the probe (b), and the probe (c).

11. The chip of claim 1, comprising:
  a hollow fiber; and
  a gel retained in a hollow of the hollow fiber and containing the probes (a), the probe (b), and the probe (c),
  wherein the chip has a thickness of from 0.01 mm to 1 mm.

12. The chip of claim 1, wherein the first probe has a sequence having at least 90% homology to the first nucleotide sequence selected from SEQ ID NOS: 6 and 7, and the second probe has a sequence having at least 90% homology to the second nucleotide sequence selected from SEQ ID NOS: 2-5.

13. The chip of claim 1, wherein the first probe has a sequence having at least 90% homology to the first nucleotide sequence selected from SEQ ID NOS: 6 and 7 or to the complementary sequence of the first nucleotide sequence, and the second probe has a sequence having at least 90% homology to the second nucleotide sequence selected from SEQ ID NOS: 2-5 or to a complementary sequence of the second nucleotide sequence.

* * * * *

```
SEQUENCE LISTING

<160> NUMBER OF SEQ ID NOS: 42

<210> SEQ ID NO 1
<211> LENGTH: 23
<212> TYPE: DNA
<213> ORGANISM: Artificial
<220> FEATURE:
<223> OTHER INFORMATION: Synthetic DNA

<400> SEQUENCE: 1
cgtattaccg cggctgctgg cac                                            23

<210> SEQ ID NO 2
<211> LENGTH: 19
<212> TYPE: DNA
<213> ORGANISM: Artificial
<220> FEATURE:
<223> OTHER INFORMATION: Synthetic DNA

<400> SEQUENCE: 2
cagtttccga tgcagttcc                                                 19

<210> SEQ ID NO 3
<211> LENGTH: 17
<212> TYPE: DNA
<213> ORGANISM: Artificial
<220> FEATURE:
<223> OTHER INFORMATION: Synthetic DNA

<400> SEQUENCE: 3
gccgtgactt gctggtt                                                   17

<210> SEQ ID NO 4
<211> LENGTH: 17
<212> TYPE: DNA
<213> ORGANISM: Artificial
<220> FEATURE:
<223> OTHER INFORMATION: Synthetic DNA

<400> SEQUENCE: 4
ctgtcctctt ctgcact                                                   17

<210> SEQ ID NO 5
<211> LENGTH: 17
<212> TYPE: DNA
<213> ORGANISM: Artificial
<220> FEATURE:
<223> OTHER INFORMATION: Synthetic DNA

<400> SEQUENCE: 5
tttcccagtt tccgatg                                                   17
```

```
<210> SEQ ID NO 6
<211> LENGTH: 18
<212> TYPE: DNA
<213> ORGANISM: Artificial
<220> FEATURE:
<223> OTHER INFORMATION: Synthetic DNA

<400> SEQUENCE: 6
ccgtcactgt gtaagctt                                                 18

<210> SEQ ID NO 7
<211> LENGTH: 18
<212> TYPE: DNA
<213> ORGANISM: Artificial
<220> FEATURE:
<223> OTHER INFORMATION: Synthetic DNA

<400> SEQUENCE: 7
ttagccgtcc ctttctgg                                                 18

<210> SEQ ID NO 8
<211> LENGTH: 18
<212> TYPE: DNA
<213> ORGANISM: Artificial
<220> FEATURE:
<223> OTHER INFORMATION: Synthetic DNA

<400> SEQUENCE: 8
cacacgttct tgacttac                                                 18

<210> SEQ ID NO 9
<211> LENGTH: 30
<212> TYPE: DNA
<213> ORGANISM: Artificial
<220> FEATURE:
<223> OTHER INFORMATION: Synthetic DNA

<400> SEQUENCE: 9
cgtgcattgt cgtgtaggtt cgaccctaat                                    30

<210> SEQ ID NO 10
<211> LENGTH: 30
<212> TYPE: DNA
<213> ORGANISM: Artificial
<220> FEATURE:
<223> OTHER INFORMATION: Synthetic DNA

<400> SEQUENCE: 10
gcagctacgt tcatacctac gcaaggcatt                                    30

<210> SEQ ID NO 11
<211> LENGTH: 30
<212> TYPE: DNA
<213> ORGANISM: Artificial
<220> FEATURE:
<223> OTHER INFORMATION: Synthetic DNA

<400> SEQUENCE: 11
gaggagatac cgaatcggtc gacgacattt                                    30

<210> SEQ ID NO 12
<211> LENGTH: 30
<212> TYPE: DNA
<213> ORGANISM: Artificial
<220> FEATURE:
<223> OTHER INFORMATION: Synthetic DNA
```

```
<400> SEQUENCE: 12
tgttgcgtga aggtcgtgaa cgattggcaa                                    30

<210> SEQ ID NO 13
<211> LENGTH: 30
<212> TYPE: DNA
<213> ORGANISM: Artificial
<220> FEATURE:
<223> OTHER INFORMATION: Synthetic DNA

<400> SEQUENCE: 13
cccctactga gcaaacgttg cactaatgga                                    30

<210> SEQ ID NO 14
<211> LENGTH: 30
<212> TYPE: DNA
<213> ORGANISM: Artificial
<220> FEATURE:
<223> OTHER INFORMATION: Synthetic DNA

<400> SEQUENCE: 14
aacaacgacc gagtgcatag tcacgtacga                                    30

<210> SEQ ID NO 15
<211> LENGTH: 30
<212> TYPE: DNA
<213> ORGANISM: Artificial
<220> FEATURE:
<223> OTHER INFORMATION: Synthetic DNA

<400> SEQUENCE: 15 aggagccctaaggtattggc gagaaaagtc                                     30

<210> SEQ ID NO 16
<211> LENGTH: 30
<212> TYPE: DNA
<213> ORGANISM: Artificial
<220> FEATURE:
<223> OTHER INFORMATION: Synthetic DNA

<400> SEQUENCE: 16
ctgagtatcc gcatatcttc cgaggttgca                                    30

<210> SEQ ID NO 17
<211> LENGTH: 30
<212> TYPE: DNA
<213> ORGANISM: Artificial
<220> FEATURE:
<223> OTHER INFORMATION: Synthetic DNA

<400> SEQUENCE: 17
acttagctga ccgaaggacc ataacgctgt                                    30

<210> SEQ ID NO 18
<211> LENGTH: 30
<212> TYPE: DNA
<213> ORGANISM: Artificial
<220> FEATURE:
<223> OTHER INFORMATION: Synthetic DNA

<400> SEQUENCE: 18
tggaagggat ccgtagtcaa ccgttgactt                                    30

<210> SEQ ID NO 19
```

<211> LENGTH: 30
<212> TYPE: DNA
<213> ORGANISM: Artificial
<220> FEATURE:
<223> OTHER INFORMATION: Synthetic DNA
<400> SEQUENCE: 19
cggatcgaca tacgacgcct acagaatgtt                                          30

<210> SEQ ID NO 20
<211> LENGTH: 30
<212> TYPE: DNA
<213> ORGANISM: Artificial
<220> FEATURE:
<223> OTHER INFORMATION: Synthetic DNA
<400> SEQUENCE: 20
taaacgtcta ggcgagacta tgagtgctcc                                          30

<210> SEQ ID NO 21
<211> LENGTH: 30
<212> TYPE: DNA
<213> ORGANISM: Artificial
<220> FEATURE:
<223> OTHER INFORMATION: Synthetic DNA
<400> SEQUENCE: 21
cgtatggatc gatccgacgt accacattag                                          30

<210> SEQ ID NO 22
<211> LENGTH: 30
<212> TYPE: DNA
<213> ORGANISM: Artificial
<220> FEATURE:
<223> OTHER INFORMATION: Synthetic DNA
<400> SEQUENCE: 22
actgcgtatg atcgacacgg ctaatcgtag                                          30

<210> SEQ ID NO 23
<211> LENGTH: 30
<212> TYPE: DNA
<213> ORGANISM: Artificial
<220> FEATURE:
<223> OTHER INFORMATION: Synthetic DNA
<400> SEQUENCE: 23
ctattcgacc agcgatatca ctacgtaggc                                          30

<210> SEQ ID NO 24
<211> LENGTH: 459
<212> TYPE: DNA
<213> ORGANISM: Artificial
<220> FEATURE:
<223> OTHER INFORMATION: Synthetic DNA
<400> SEQUENCE: 24
gtgagaagcc tacacaaacg taacgtcagg gctaagacaa acgctaacgg tacaccctag         60
atgggagctt gtagctagat cgctaagtcc taccgacatg taggcatact cacgaaggca        120
attccctgaa agcctcgtct tatcccgaac ttggcatctg ctgatacgtc aggttgaacg        180
cgtacattta cctgtcatgc gtgaatggta agggtcgtat tagggtcgaa cctacacgac        240
aatgcacgtc gaagcggttg ctaatgcaca ttggctaagg cccacggaac acgaatcacg        300
tgagatcact tactattcga cggaactact atacgcaccg ggacatgcaa gtagcgtccc        360

```
acaagcataa ggaactctat actcgccatc tacgcagcta caggggatac acgtatgagc    420
ggttacgaag taaagccgag atagagcggt ctttagaga                           459
```

<210> SEQ ID NO 25
<211> LENGTH: 459
<212> TYPE: DNA
<213> ORGANISM: Artificial
<220> FEATURE:
<223> OTHER INFORMATION: Synthetic DNA

<400> SEQUENCE: 25

```
gtgagaagcc tacacaaacg taacgtcagg gctaagacaa acgctaacgg tacaccctag     60
atgggagctt gtagctagat cgctaagtcc taccgacatg taggcatact cacgaaggca    120
attccctgaa agcctcgtct tatcccgaac ttggcatctg ctgatacgtc aggttgaacg    180
cgtacattta cctgtcatgc gtggtagccg attgaactaa tgccttgcgt aggtatgaac    240
gtagctgcta gtcgaggcct tgtatgcaca ttggctaagg cccacggaac acgaatcacg    300
tgagatcact tactattcga cggaactact atacgcaccg gacatgcaa gtagcgtccc     360 acaagcataa ggaactctat actcgccatc tacgcagcta caggggatac acgtatgagc    420
ggttacgaag taaagccgag atagagcggt ctttagaga                           459
```

<210> SEQ ID NO 26
<211> LENGTH: 459
<212> TYPE: DNA
<213> ORGANISM: Artificial
<220> FEATURE:
<223> OTHER INFORMATION: Synthetic DNA

<400> SEQUENCE: 26

```
gtgagaagcc tacacaaacg taacgtcagg gctaagacaa acgctaacgg tacaccctag     60
atgggagctt gtagctagat cgctaagtcc taccgacatg taggcatact cacgaaggca    120
attccctgaa agcctcgtct tatcccgaac ttggcatctg ctgatacgtc aggttgaacg    180
cgtacattta cctgtcatgc gtgtcctcga tacatacgaa atgtcgtcga ccgattcggt    240
atctcctctg gcaccgaaga caaatgcaca ttggctaagg cccacggaac acgaatcacg    300
tgagatcact tactattcga cggaactact atacgcaccg gacatgcaa gtagcgtccc     360 acaagcataa ggaactctat actcgccatc tacgcagcta caggggatac acgtatgagc    420
ggttacgaag taaagccgag atagagcggt ctttagaga                           459
```

<210> SEQ ID NO 27
<211> LENGTH: 459
<212> TYPE: DNA
<213> ORGANISM: Artificial
<220> FEATURE:
<223> OTHER INFORMATION: Synthetic DNA

<400> SEQUENCE: 27

```
gtgagaagcc tacacaaacg taacgtcagg gctaagacaa acgctaacgg tacaccctag     60
atgggagctt gtagctagat cgctaagtcc taccgacatg taggcatact cacgaaggca    120
attccctgaa agcctcgtct tatcccgaac ttggcatctg ctgatacgtc aggttgaacg    180
cgtacattta cctgtcatgc gtgtgctacg ctttacgctt gccaatcgtt cacgaccttc    240
acgcaacact tgatcgaacc gaaatgcaca ttggctaagg cccacggaac acgaatcacg    300
tgagatcact tactattcga cggaactact atacgcaccg gacatgcaa gtagcgtccc     360
```

| | |
|---|---|
| acaagcataa ggaactctat actcgccatc tacgcagcta caggggatac acgtatgagc | 420 |
| ggttacgaag taaagccgag atagagcggt ctttagaga | 459 |

<210> SEQ ID NO 28
<211> LENGTH: 459
<212> TYPE: DNA
<213> ORGANISM: Artificial
<220> FEATURE:
<223> OTHER INFORMATION: Synthetic DNA

<400> SEQUENCE: 28

| | |
|---|---|
| gtgagaagcc tacacaaacg taacgtcagg gctaagacaa acgctaacgg tacaccctag | 60 |
| atgggagctt gtagctagat cgctaagtcc taccgacatg taggcatact cacgaaggca | 120 |
| attccctgaa agcctcgtct tatcccgaac ttggcatctg ctgatacgtc aggttgaacg | 180 |
| cgtacattta cctgtcatgc gtgacaacag acggtacgtc cattagtgca acgtttgctc | 240 |
| agtaggggt ctaagcgtca cttatgcaca ttggctaagg cccacggaac acgaatcacg | 300 |
| tgagatcact tactattcga cggaactact atacgcaccg ggacatgcaa gtagcgtccc | 360 |
| acaagcataa ggaactctat actcgccatc tacgcagcta caggggatac acgtatgagc | 420 |
| ggttacgaag taaagccgag atagagcggt ctttagaga | 459 |

<210> SEQ ID NO 29
<211> LENGTH: 459
<212> TYPE: DNA
<213> ORGANISM: Artificial
<220> FEATURE:
<223> OTHER INFORMATION: Synthetic DNA

<400> SEQUENCE: 29

| | |
|---|---|
| gtgagaagcc tacacaaacg taacgtcagg gctaagacaa acgctaacgg tacaccctag | 60 |
| atgggagctt gtagctagat cgctaagtcc taccgacatg taggcatact cacgaaggca | 120 |
| attccctgaa agcctcgtct tatcccgaac ttggcatctg ctgatacgtc aggttgaacg | 180 |
| cgtacattta cctgtcatgc gtgggagcag ttttcttctc gtacgtgact atgcactcgg | 240 |
| tcgttgttgg aataccggtc gtaatgcaca ttggctaagg cccacggaac acgaatcacg | 300 |
| tgagatcact tactattcga cggaactact atacgcaccg ggacatgcaa gtagcgtccc | 360 |
| acaagcataa ggaactctat actcgccatc tacgcagcta caggggatac acgtatgagc | 420 |
| ggttacgaag taaagccgag atagagcggt ctttagaga | 459 |

<210> SEQ ID NO 30
<211> LENGTH: 459
<212> TYPE: DNA
<213> ORGANISM: Artificial
<220> FEATURE:
<223> OTHER INFORMATION: Synthetic DNA

<400> SEQUENCE: 30

| | |
|---|---|
| gtgagaagcc tacacaaacg taacgtcagg gctaagacaa acgctaacgg tacaccctag | 60 |
| atgggagctt gtagctagat cgctaagtcc taccgacatg taggcatact cacgaaggca | 120 |
| attccctgaa agcctcgtct tatcccgaac ttggcatctg ctgatacgtc aggttgaacg | 180 |
| cgtacattta cctgtcatgc gtgaacgcaa tacggtggga cttttctcgc caataccta | 240 |
| gggctcctgt gtacctaagc gaaatgcaca ttggctaagg cccacggaac acgaatcacg | 300 |
| tgagatcact tactattcga cggaactact atacgcaccg ggacatgcaa gtagcgtccc | 360 |
| acaagcataa ggaactctat actcgccatc tacgcagcta caggggatac acgtatgagc | 420 |

```
ggttacgaag taaagccgag atagagcggt ctttagaga                           459
```

<210> SEQ ID NO 31
<211> LENGTH: 459
<212> TYPE: DNA
<213> ORGANISM: Artificial
<220> FEATURE:
<223> OTHER INFORMATION: Synthetic DNA

<400> SEQUENCE: 31

```
gtgagaagcc tacacaaacg taacgtcagg gctaagacaa acgctaacgg tacaccctag    60
atgggagctt gtagctagat cgctaagtcc taccgacatg taggcatact cacgaaggca   120
attccctgaa agcctcgtct tatcccgaac ttggcatctg ctgatacgtc aggttgaacg   180
cgtacattta cctgtcatgc gtgggatgac ggataagttg caacctcgga agatatgcgg   240
atactcagac gtgatatgcg cagatgcaca ttggctaagg cccacggaac acgaatcacg   300
tgagatcact tactattcga cggaactact atacgcaccg ggacatgcaa gtagcgtccc   360
acaagcataa ggaactctat actcgccatc tacgcagcta caggggatac acgtatgagc   420
ggttacgaag taaagccgag atagagcggt ctttagaga                          459
```

<210> SEQ ID NO 32
<211> LENGTH: 459
<212> TYPE: DNA
<213> ORGANISM: Artificial
<220> FEATURE:
<223> OTHER INFORMATION: Synthetic DNA

<400> SEQUENCE: 32

```
gtgagaagcc tacacaaacg taacgtcagg gctaagacaa acgctaacgg tacaccctag    60
atgggagctt gtagctagat cgctaagtcc taccgacatg taggcatact cacgaaggca   120
attccctgaa agcctcgtct tatcccgaac ttggcatctg ctgatacgtc aggttgaacg   180
cgtacattta cctgtcatgc gtgggtgtac atcggatgac agcgttatgg tccttcggtc   240
agctaagtaa gtccgttttc cacatgcaca ttggctaagg cccacggaac acgaatcacg   300
tgagatcact tactattcga cggaactact atacgcaccg ggacatgcaa gtagcgtccc   360
acaagcataa ggaactctat actcgccatc tacgcagcta caggggatac acgtatgagc   420
ggttacgaag taaagccgag atagagcggt ctttagaga                          459
```

<210> SEQ ID NO 33
<211> LENGTH: 459
<212> TYPE: DNA
<213> ORGANISM: Artificial
<220> FEATURE:
<223> OTHER INFORMATION: Synthetic DNA

<400> SEQUENCE: 33

```
gtgagaagcc tacacaaacg taacgtcagg gctaagacaa acgctaacgg tacaccctag    60
atgggagctt gtagctagat cgctaagtcc taccgacatg taggcatact cacgaaggca   120
attccctgaa agcctcgtct tatcccgaac ttggcatctg ctgatacgtc aggttgaacg   180
cgtacattta cctgtcatgc gtgttcagtc aaccggagaa gtcaacggtt gactacggat   240
cccttccatg tagagctctc acaatgcaca ttggctaagg cccacggaac acgaatcacg   300
tgagatcact tactattcga cggaactact atacgcaccg ggacatgcaa gtagcgtccc   360
acaagcataa ggaactctat actcgccatc tacgcagcta caggggatac acgtatgagc   420
```

```
ggttacgaag taaagccgag atagagcggt ctttagaga                        459
```

<210> SEQ ID NO 34
<211> LENGTH: 459
<212> TYPE: DNA
<213> ORGANISM: Artificial
<220> FEATURE:
<223> OTHER INFORMATION: Synthetic DNA

<400> SEQUENCE: 34

```
gtgagaagcc tacacaaacg taacgtcagg gctaagacaa acgctaacgg tacaccctag   60
atgggagctt gtagctagat cgctaagtcc taccgacatg taggcatact cacgaaggca  120
attccctgaa agcctcgtct tatcccgaac ttggcatctg ctgatacgtc aggttgaacg  180
cgtacattta cctgtcatgc gtggcgattg tcgcgttaaa cattctgtag gcgtcgtatg  240
tcgatccggg acttcgcttc ataatgcaca ttggctaagg cccacggaac acgaatcacg  300
tgagatcact tactattcga cggaactact atacgcaccg ggacatgcaa gtagcgtccc  360
acaagcataa ggaactctat actcgccatc tacgcagcta caggggatac acgtatgagc  420
ggttacgaag taaagccgag atagagcggt ctttagaga                        459
```

<210> SEQ ID NO 35
<211> LENGTH: 459
<212> TYPE: DNA
<213> ORGANISM: Artificial
<220> FEATURE:
<223> OTHER INFORMATION: Synthetic DNA

<400> SEQUENCE: 35

```
gtgagaagcc tacacaaacg taacgtcagg gctaagacaa acgctaacgg tacaccctag   60
atgggagctt gtagctagat cgctaagtcc taccgacatg taggcatact cacgaaggca  120
attccctgaa agcctcgtct tatcccgaac ttggcatctg ctgatacgtc aggttgaacg  180
cgtacattta cctgtcatgc gtgtcgtgtg tcgtgagagg agcactcata gtctcgccta  240
gacgtttatg acgagatatc acgatgcaca ttggctaagg cccacggaac acgaatcacg  300
tgagatcact tactattcga cggaactact atacgcaccg ggacatgcaa gtagcgtccc  360
acaagcataa ggaactctat actcgccatc tacgcagcta caggggatac acgtatgagc  420
ggttacgaag taaagccgag atagagcggt ctttagaga                        459
```

<210> SEQ ID NO 36
<211> LENGTH: 459
<212> TYPE: DNA
<213> ORGANISM: Artificial
<220> FEATURE:
<223> OTHER INFORMATION: Synthetic DNA

<400> SEQUENCE: 36

```
gtgagaagcc tacacaaacg taacgtcagg gctaagacaa acgctaacgg tacaccctag   60
atgggagctt gtagctagat cgctaagtcc taccgacatg taggcatact cacgaaggca  120
attccctgaa agcctcgtct tatcccgaac ttggcatctg ctgatacgtc aggttgaacg  180
cgtacattta cctgtcatgc gtggtagcgt gtaacgcact aatgtggtac gtcggatcga  240
tccatacgca actttgtacc gagatgcaca ttggctaagg cccacggaac acgaatcacg  300
tgagatcact tactattcga cggaactact atacgcaccg ggacatgcaa gtagcgtccc  360
acaagcataa ggaactctat actcgccatc tacgcagcta caggggatac acgtatgagc  420
ggttacgaag taaagccgag atagagcggt ctttagaga                        459
```

<210> SEQ ID NO 37
<211> LENGTH: 459
<212> TYPE: DNA
<213> ORGANISM: Artificial
<220> FEATURE:
<223> OTHER INFORMATION: Synthetic DNA

<400> SEQUENCE: 37

| | | | | | |
|---|---|---|---|---|---|
| gtgagaagcc | tacacaaacg | taacgtcagg | gctaagacaa | acgctaacgg | tacaccctag | 60 |
| atgggagctt | gtagctagat | cgctaagtcc | taccgacatg | taggcatact | cacgaaggca | 120 |
| attccctgaa | agcctcgtct | tatcccgaac | ttggcatctg | ctgatacgtc | aggttgaacg | 180 |
| cgtacattta | cctgtcatgc | gtgagcaacc | atcttgagct | acgattagcc | gtgtcgatca | 240 |
| tacgcagtcc | gaggcattac | tgaatgcaca | ttggctaagg | cccacggaac | acgaatcacg | 300 |
| tgagatcact | tactattcga | cggaactact | atacgcaccg | ggacatgcaa | gtagcgtccc | 360 |
| acaagcataa | ggaactctat | actcgccatc | tacgcagcta | cagggatac | acgtatgagc | 420 |
| ggttacgaag | taaagccgag | atagagcggt | ctttagaga | | | 459 |

<210> SEQ ID NO 38
<211> LENGTH: 459
<212> TYPE: DNA
<213> ORGANISM: Artificial
<220> FEATURE:
<223> OTHER INFORMATION: Synthetic DNA

<400> SEQUENCE: 38

| | | | | | |
|---|---|---|---|---|---|
| gtgagaagcc | tacacaaacg | taacgtcagg | gctaagacaa | acgctaacgg | tacaccctag | 60 |
| atgggagctt | gtagctagat | cgctaagtcc | taccgacatg | taggcatact | cacgaaggca | 120 |
| attccctgaa | agcctcgtct | tatcccgaac | ttggcatctg | ctgatacgtc | aggttgaacg | 180 |
| cgtacattta | cctgtcatgc | gtgggccttc | tccgaatagc | ctacgtagtg | atatcgctgg | 240 |
| tcgaataggc | ggattgctca | taaatgcaca | ttggctaagg | cccacggaac | acgaatcacg | 300 |
| tgagatcact | tactattcga | cggaactact | atacgcaccg | ggacatgcaa | gtagcgtccc | 360 |
| acaagcataa | ggaactctat | actcgccatc | tacgcagcta | cagggatac | acgtatgagc | 420 |
| ggttacgaag | taaagccgag | atagagcggt | ctttagaga | | | 459 |

<210> SEQ ID NO 39
<211> LENGTH: 25
<212> TYPE: DNA
<213> ORGANISM: Artificial
<220> FEATURE:
<223> OTHER INFORMATION: Synthetic DNA

<400> SEQUENCE: 39
gagaagccta cacaaacgta acgtc         25

<210> SEQ ID NO 40
<211> LENGTH: 23
<212> TYPE: DNA
<213> ORGANISM: Artificial
<220> FEATURE:
<223> OTHER INFORMATION: Synthetic DNA

<400> SEQUENCE: 40
ctctaaagac cgctctatct cgg           23

<210> SEQ ID NO 41

```
<211> LENGTH: 15
<212> TYPE: DNA
<213> ORGANISM: Artificial
<220> FEATURE:
<223> OTHER INFORMATION: Synthetic DNA

<400> SEQUENCE: 41
tacgggaggc agcag                                                    15

<210> SEQ ID NO 42
<211> LENGTH: 19
<212> TYPE: DNA
<213> ORGANISM: Artificial
<220> FEATURE:
<223> OTHER INFORMATION: Synthetic DNA

<400> SEQUENCE: 42
crgggtatct aatccygtt                                                19
```